(12) United States Patent
Mirmehrabi

(10) Patent No.: US 10,556,922 B2
(45) Date of Patent: Feb. 11, 2020

(54) CRYSTALLINE AND AMORPHOUS FORMS OF 17-ALPHA-HYDROXYPROGESTERONE CAPROATE

(71) Applicant: AMAG Pharmaceuticals, Inc., Waltham, MA (US)

(72) Inventor: Mahmoud Mirmehrabi, Halifax (CA)

(73) Assignee: AMAG PHARMACEUTICALS, INC., Waltham, MA (US)

( * ) Notice: Subject to any disclaimer, the term of this patent is extended or adjusted under 35 U.S.C. 154(b) by 0 days.

(21) Appl. No.: 15/764,100

(22) PCT Filed: Sep. 29, 2016

(86) PCT No.: PCT/US2016/054446
§ 371 (c)(1),
(2) Date: Mar. 28, 2018

(87) PCT Pub. No.: WO2017/059070
PCT Pub. Date: Apr. 6, 2017

(65) Prior Publication Data
US 2018/0282366 A1    Oct. 4, 2018

Related U.S. Application Data

(60) Provisional application No. 62/234,280, filed on Sep. 29, 2015.

(51) Int. Cl.
*C07J 7/00* (2006.01)
*A61K 31/56* (2006.01)
*A61K 9/10* (2006.01)
*A61K 47/44* (2017.01)
*A61P 43/00* (2006.01)
*A61K 9/00* (2006.01)

(52) U.S. Cl.
CPC ............... *C07J 7/0045* (2013.01); *A61K 9/10* (2013.01); *A61K 31/56* (2013.01); *A61K 47/44* (2013.01); *A61P 43/00* (2018.01); *A61K 9/0014* (2013.01); *A61K 9/0019* (2013.01); *A61K 9/0053* (2013.01); *C07B 2200/13* (2013.01)

(58) Field of Classification Search
None
See application file for complete search history.

(56) References Cited

U.S. PATENT DOCUMENTS 3,758,687 A    9/1973    Ufer et al.
5,906,830 A    5/1999    Farinas et al.
(Continued)

FOREIGN PATENT DOCUMENTS

CN      103582484 A        2/2014
WO    WO-2003/068186 A1    8/2003
(Continued)

OTHER PUBLICATIONS

Kirk-Othmer Encyclopedia of Chemical Technology Copyright © 2002 by John Wiley & Sons, Inc., pp. 95-147, Article Online Posting Date: Aug. 16, 2002 (Year: 2002).*
(Continued)

*Primary Examiner* — Karl J Puttlitz
(74) *Attorney, Agent, or Firm* — Goodwin Procter LLP

(57) ABSTRACT

The disclosure is in part directed to crystalline forms of 17-α-hydroxyprogesterone caproate and variants thereof.

22 Claims, 8 Drawing Sheets

(56) References Cited

U.S. PATENT DOCUMENTS

| | | | |
|---|---|---|---|
| 6,117,446 | A | 9/2000 | Place |
| 6,200,593 | B1 | 3/2001 | Place |
| 6,221,379 | B1 | 4/2001 | Place |
| 6,241,529 | B1 | 6/2001 | Place |
| 6,284,263 | B1 | 9/2001 | Place |
| 6,745,962 | B2 | 6/2004 | Reed et al. |
| 6,991,191 | B2 | 1/2006 | Reed et al. |
| 7,879,360 | B2 | 2/2011 | Cunningham et al. |
| 7,884,093 | B2 | 2/2011 | Creasy et al. |
| 8,268,352 | B2 | 9/2012 | Vaya et al. |
| 8,828,981 | B2 | 9/2014 | Creasy et al. |
| 8,951,996 | B2 | 2/2015 | Giliyar et al. |
| 9,421,333 | B2 | 8/2016 | Wotton et al. |
| 9,844,558 | B1 | 12/2017 | Birch et al. |
| 2005/0051401 | A1 | 3/2005 | Shimazaki et al. |
| 2008/0188829 | A1 | 8/2008 | Creasy |
| 2009/0053294 | A1 | 2/2009 | Prendergast |
| 2010/0041906 | A1 | 2/2010 | Van Boxtel et al. |
| 2010/0278725 | A1 | 11/2010 | Liu et al. |
| 2011/0152840 | A1 | 6/2011 | Lee et al. |
| 2011/0262502 | A1 | 10/2011 | Lee et al. |
| 2014/0030556 | A1 | 1/2014 | Beer |
| 2014/0271882 | A1 | 9/2014 | Giliyar et al. |
| 2014/0303556 | A1 | 10/2014 | Travanty |
| 2014/0377317 | A1 | 12/2014 | Giliyar et al. |
| 2015/0165049 | A1 | 6/2015 | Giliyar et al. |

FOREIGN PATENT DOCUMENTS

| | | | |
|---|---|---|---|
| WO | WO-2005/044234 | A2 | 5/2005 |
| WO | WO-2005/051401 | A2 | 6/2005 |
| WO | WO-2007/049265 | A2 | 5/2007 |
| WO | WO-2007/114948 | A2 | 10/2007 |
| WO | WO-2008/096122 | A2 | 8/2008 |
| WO | WO-2011/079047 | A1 | 6/2011 |
| WO | WO-2013/016697 | A2 | 1/2013 |
| WO | WO-2013/067346 | A1 | 5/2013 |

OTHER PUBLICATIONS

Rouhi, "The Right Stuff, from research and development to the clinic, getting drug crystals right is full of pitfalls", Chemical & Engineering News, Feb. 24, 2003, pp. 32-35 (Year: 2003).*
Rajnikant et al., J Chem Crystallogr (2008) 38:211-230 (Year: 2008).*
Database Caplus Chemical Abstracts Service, Columbus, Ohio, US; Database Accession No. 1989:183487, Abstract of Krstanovic et al., Acta Crystallographica, Section C: Crystal Structure Communications (1989), C45(3), 478-80 (Year: 1989).*
Abboud, et al. "Effect of Progesterone, Its Hydroxylated and Methylated Derivatives, and Dydrogesterone on Lipid Bilayer Membranes." The Journal of membrane biology (2015): 1-14.
Anderson BL et al., (2007) 'Idiopathic Vertebral Abscess in Pregnancy: Case Report and Literature Review,' Am J Perintology, 24(6):377-9.
Anderson L et al., (2009) 'The Effect of Progesterone on Myometrial Contractility, Potassium Channels, and Tocolytic Efficacy,' Reprod Sci, Jul. 14, 2009 (ePub), 16(11):1052-61.
Anonymous (1957) 'New and Nonofficial Remedies—Hydroxyprogesterone Caproate,' Council on Pharmacy and Chemistry (Eds), J Am Med Assoc. 163(5):356-7.
Anonymous, (2006) 'Preterm Birth: Causes, Consequences, and Prevention,' Report Brief • Jul. 2006, Institute of Medicine, Washington, DC (Publ) (4 pages).
Anonymous, (2006), 'N.48: Asthma,' In: 'The Merck Manual of Diagnosis and Therapy,' (18th Ed, 2006),<http://scholar.google.com/scholar?q=>, Merck Research Laboratories, NJ, (Publ), XP002630480, ISBN: 0911910182 pp. 381-99, the whole document.
Anonymous, (2008), 'Use of Progesterone to Reduce Preterm Birth,' Committee Opinion No. 419, Committee on Obstetric Practice (Eds), The American College of Obstetricians and Gynecologists, Washington, DC (Publ), 112(4):963-5.
Anonymous, (2013), 'Highlights of Prescribing Information . . . for Makena® (hydroxyprogesterone caproate Injection) for Intramuscular Use,' Hospira, Inc., Lake Forest, IL (Pub) (4 pages).
Armstrong J, (2007) '17 Progesterone for Preterm Birth Prevention: A Potential 2 Billion Dollar Opportunity,' Am J Obstet Gynecol, 196(3):194-5.
Bailit JL and Votruba ME, (2007) 'Medical Cost Savings Associated with 17 Alpha-Hydroxyprogesterone Caproate,' Am J Obstet Gynecol, 196(3):219.e1-7.
Battaglia FC and Lubchenco LO, (1967) 'A Practical Classification of Newborn Infants by Weight and Gestational Age,' J Pediatr, 71(2):159-63.
Berghella V et al., (2010) '17-Alpha-Hydroxyprogesterone Caproate for the Prevention of Preterm Birth in Women with Prior Preterm Birth and a Short Cervical Length,' Am J Obstet Gynecol, 202(4):351. e1-6.
Berghella V, (2009), 'Novel Developments on Cervical Length Screening and Progesterone for Preventing Preterm Birth,' BJOG, 116:182-7.
Bernstein PS, (2008) 'Withdrawal of 17 Alpha-Hydroxyprogesterone: A Possible Trigger for Preterm Labor?,' Am J Obstet Gynecol, 198(2):244.
Brancazio LR et al., (2003) 'Prevention of Recurrent Preterm Delivery by 17 Alpha-Hydroxyprogesterone Caproate,' N Engl J Med, 349(11):1087-8.
Breart G et al., (1979) 'A Comparative Study of the Efficiency of Hydroxyprogesterone Caproate and of Chlormadinone Acetate in the Prevention of Premature Labor,' Int J Gynaecol Obstet, 16(5):381-4.
Briery CM et al., (2009) 'Progesterone Does not Prevent Preterm Births in Women with Twins,' South Med J, 102(9):900-4.
Briery CM et al., (2011) 'Women with Preterm Premature Rupture of the Membranes do not Benefit from Weekly Progesterone,' Am J Obstet Gynecol, 204(1):54.e1-5.
Cahill AG et al., (2010), 'Universal Cervical Length Screening and Treatment with Vaginal Progesterone to Prevent Preterm Birth: A Decision and Economic Analysis,' Am J Obstet Gynecol, Jan. 15, 2010 (ePub), 202(6):548.
Cartitis SN et al., (2009) 'Prevention of Preterm Birth in Triplets Using 17 Alpha-Hydroxyprogesterone Caproate: A Randomized Controlled Trial,' Obstet Gynecol, 113(2 Pt 1):285-92.
Chao AS et al., (2008) 'Ultrasound Assessment of Cervical Length in Pregnancy,' Taiwan J Obstet Gynecol, 47(3):291-5.
Christian MS et al., (2007) 'Embryo-fetal Toxicity Signals for 17Alpha-Hydroxyprogesterone Caproate in High-Risk Pregnancies: A Review of the Non-Clinical Literature for Embryo-fetal Toxicity with Progestins,' J Matern Fetal Neonatal Med, 20(2):89-112.
Cnattingius S, (2004) 'The Epidemiology of Smoking During Pregnancy: Smoking Prevalence, Maternal Characteristics, and Pregnancy Outcomes,' Nicotine Tob Res, (6)2:S125-40.
Combs CA et al., (2010) 'Failure of 17-Hydroxyprogesterone to Reduce Neonatal Morbidity or Prolong Triplet Pregnancy: A Double-Blind, Randomized Clinical Trial,' Am J Obstet Gynecol, 203(3):248. e1-9.
Creasy RK and Herron MA, (1981) 'Prevention of Preterm Birth,' Semin Perinatol, 5(3):295-302.
Cypher R, (2007) 'Gestiva for Preventing Prematurity: A New View of an Old Therapy,' Nurs Womens Health,11(3):322-5.
Da Fonseca EB et al., (2003) 'Prophylactic Administration of Progesterone by Vaginal Suppository to Reduce the Incidence of Spontaneous Preterm Birth in women at Increased Risk: A Randomized Placebo-Controlled Double-Blind Study,' Am J Obstet Gynecol, 188(2):419-24.
Davis ME and Plotz EJ, (1957) 'The Metabolism of Progesterone and its Clinical Use in Pregnancy,' Recent Prog Horm Res, 13:347-79.
Davis ME and Wied GL, (1955) '17-Alpha-Hydroxyprogesterone-Caproate: A New Substance with Prolonged Progestational Activity; a Comparison with Chemically Pure Progesterone,' J Clin Endocrinol Metab, 15(8):923-30.

(56) References Cited

OTHER PUBLICATIONS

Davis ME and Wied GL, (1957) 'Long-Acting Progestational Agents; 17-Ethinyl-19-Nortestosterone Enanthate, 17 Alpha-Hydroxyprogesterone Caproate and 17-Alpha-Hydroxy-Progesterone Acetate,' Geburtshilfe Frauenheilkd, 17(10):916-28.
Dodd JM et al., (2005) 'Progesterone Supplementation for Preventing Preterm Birth: A Systematic Review and Meta-Analysis,' Acta Obstet Gynecol Scand, 84(6):526-33.
Dodd JM et al., (2013) 'Prenatal Administration of Progesterone for Preventing Preterm Birth in Women Considered to be at Risk of Preterm Birth,' Cochrane Database Syst Rev. Jul. 2013 31;(7):CD004947.
Doggrell SA, (2003) 'Recurrent Hope for the Treatment of Preterm Delivery,' Expert Opin Pharmacother, 4(12):2363-6.
Dubin N et al., (1979) 'Serum Progesterone and Estradiol in Pregnant Women Selected for Progestagen Treatment,' Int J Fertil, 24(2):86-93.
Durnwald CP et al., (2009) 'The Effect of Treatment with 17 Alpha-Hydroxyprogesterone Caproate on Changes in Cervical Length Over Time,' Am J Obstet Gynecol, Aug. 28, 2009 (ePub), 201(4):410.
Durnwald CP et al., (2010) 'Second Trimester Cervical Length and Risk of Preterm Birth in Women with Twin Gestations Treated with 17-? Hydroxyprogesterone Caproate,' J Matern Fetal Neonatal Med, May 4, 2010 (May 4, 2010) (ePub), 23(12):1360-4.
Elovitz MA and Mrinalini C, (2006) 'The Use of Progestational Agents for Preterm Birth: Lessons from a Mouse Model,' Am J Obstet Gynecol, 195(4):1004-10.
Facchinetti F and Vacarro V, (2009) 'Pharmacological Use of Progesterone and 17-Alpha-Hydroxyprogesterone Caproate in the Prevention of Preterm Delivery,' Minerva Ginecol, 61(5):401-9.
Facchinetti F et al., (2007) 'Cervical Length Changes During Preterm Cervical Ripening: Effects of 17-Alpha-Hydroxyprogesterone Caproate,' Am J Obstet Gynecol, 196(5):453.e1-4.
Facchinetti F et al., (2008) 17-Alpha-Hydroxy-Progesterone Effects on Cervical Proinflammatory Agents in Women at Risk for Preterm Delivery, Am J Perinatol. Aug. 28, 2008 (ePub), 25(8):503-6.
Facchinetti F et al.,(2005) 'Polyunsaturated Fatty Acids and Risk of Preterm Delivery,' Eur Rev Med Pharmacol Sci, 9(1):41-8.
Facchinetti F, (2010) '17-Alpha Hydroprogesterone Caproate and Cervical Changes,' Am J Obstet Gynec, Letters to the Editors, Sep. 2010:e9 (Letter).
Farine D et al., (2008) 'The Use of Progesterone for Prevention of Preterm Birth,' J Obstet Gynaecol Can, 30(1):67-77.
Goldenberg RL et al., (1998) 'The Preterm Prediction Study: The Value of New vs Standard Risk Factors in Predicting Early and all Spontaneous Preterm Births,' Am J Public Health, 88(2):233-8.
Goldstein P et al., (1989) 'A Meta-Analysis of Randomized Control Trials of Progestational Agents in Pregnancy,' Br J Obstet Gynaecol, 96(3):265-74.
Goldzieher J, (1961) 'Symposium on Steroid Hormones. 1. Synthetic Progestational Steroids. Their Significance and Use,' Tex State J Med, 57(12):962-7.
González-Quintero VH et al., (2007) 'Gestational Age at Initiation of 17-Hydroxyprogesterone Caproate (17P) and Recurrent Preterm Delivery,' J Matern Fetal Neonatal Med, 20(3):249-52.
González-Quintero VH et al., (2010) 'Impact of Prior Gestational Age at Preterm Delivery on Effectiveness of 17-Alpha-Hydroxyprogesterone Caproate in Practice,' Am J Obstet Gynecol, Aug. 1, 2010 (ePub), 203(3):257.e1-5.
Greene MF, (2003) 'Progesterone and Preterm Delivery—deja vu all Over Again,' N Engl J Med, 348(24):2453-5.
Haas DM and Ramsey PS, (2008) 'Progestogen for Preventing Miscarriage,' Cochrane DB Syst Rev, Apr. 16, 2008 (Apr. 16, 2008), (2):CD003511 (Abstract).
Halpern et al., Contraception vol. 86, p. 315. Published 2012 (abstract provided).
Hartikainen-Sorri A-L et al., (1980), 'Inefficacy of 17-α-Hydroxyprogesterone Caproate in the Prevention of Prematurity in Twin Pregnancies,' Obstet Gynecol, 56(6):692-5.

Hauth JC et al., (1983) 'The Effect of 17-α-Hydroxyprogesterone Caproate on Pregnancy in an Active Duty Military Population,' Am J Obstet Gynecol, 146(2):187-90.
Henderson ZT et al.,(2009) 'Attitudes and Practices Regarding Use of Progesterone to Prevent Preterm Births,' Am J Perinatol, Mar. 19, 2009 (ePub), 26(7):529-36.
How HY and Sibai BM, (2009) 'Progesterone for the Prevention of Preterm Birth: Indications, When to Initiate, Efficacy and Safety,' Ther Clin Risk Manag, Mar. 26, 2009 (ePub), 5(1):55-64 Epub Mar. 26, 2009.
How HY et al., (2007) 'Prophylaxis with 17 Alpha-Hydroxyprogesterone Caproate for Prevention of Recurrent Preterm Delivery: Does Gestational Age at Initiation of Treatment Matter?,' Am J Obstet Gynecol, 197(3):260.e1-4.
Iams JD, (2010) 'Was the Preterm Birth Rate in the Placebo Group too High in the Meis MFMU Network Trial of 17-OHPC?,' Am J Obstet Gynecol, 202(5):409-10.
International Preliminary Report on Patentability for International Application No. PCT/US2016/054446 dated Apr. 3, 2018 (8 pages).
International Search Report and Written Opinion of the International Searching Authority for International Application No. PCT/US2016/054446 dated Dec. 12, 2016 (10 pages).
International Search Report and Written Opinion of the International Searching Authority for International Application No. PCT/US2017/032816 dated Aug. 25, 2017 (9 pages).
International Searching Authority, International Search Report (Form ISA/210) for International Application No. PCT/US2010/061078 dated Apr. 28, 2011 (dated Apr. 28, 2011) (4 pages).
International Searching Authority, Written Opinion of the International Searching Authority International Search Report (Form ISA/237) for International Application No. PCT/US2010/061078 dated Apr. 28, 2011 (dated Apr. 28, 2011) (12 pages).
Ito K et al., (2001) 'Cigarette Smoking Reduces Histone Deacetylase 2 Expression, Enhances Cytokine Expression, and Inhibits Glucocorticoid Actions in Alveolar Macrophages,' FASEB J, 15(6):1110-2.
Johnson JW et al., (1979) 'High-Risk Prematurity-Progestin Treatment and Steroid Studies,' Obstet Gynecol, 54(4):412-8.
Johnson JW et al.,(1975) 'Efficacy of 17 Alpha-Hydroxyprogesterone Caproate in the Prevention of Premature Labor,' N Engl J Med, 293(14):675-80.
Joy S et al., (2010) 'The Risk for Preterm Labor in Women Receiving 17-alpha-Hydroxyprogesterone Caproate Prophylaxis for Preterm Birth Prevention,' Am J Perintol, Dec. 10, 2009 (Dec. 10, 2009) (ePub), 27(4):343-8.
Kauppila A et al., (1980) 'Suppression of Threatened Premature Labor by Administration of Cortisol and 17 Alpha-Hydroxyprogesterone Caproate: A Comparison with Ritodrine,' Am J Obstet Gynecol, 138(4):404-8.
Kautz HD, (1957) 'New and Nonofficial Remedies—Hydroxyprogesterone Caproate,' Council on Pharmacy and Chemistry (Eds), J Am Med Assoc, 163(5):356-7.
Keeler SM et al., (2009) 'A Randomized Trial of Cerclage vs. 17 Alpha-Hydroxyprogesterone Caproate for Treatment of Short Cervix,' J Perinat Med, 37(5):473-9.
Keirse MJ, (1990) 'Progestogen Administration in Pregnancy may Prevent Preterm Delivery,' Br J Obstet Gynaecol, 97(2):149-54.
Kessler WB and Borman A,(1958) 'Some Biological Activities of Certain Progestogens. I. 17 Alpha-Hydroxyprogesterone 17-n-Caproate,' Ann N Y Acad Sci, 71(5):486-93.
Klebanoff MA, (2007) 'Subgroup Analysis in Obstetrics Clinical Trials,' Am J Obstet Gynecol, 197(2):119-22.
Kuon RJ et al., (2010) 'Pharmacologic Actions of Progestins to Inhibit Cervical Ripening and Prevent Delivery Depend on Their Properties, the Route of Administration, and the Vehicle,' Am J Obstet Gynecol, 202(5):455.e1-9.
Kuon, et al. "Actions of progestins for the inhibition of cervical ripening and uterine contractions to prevent preterm birth." Facts, views & vision in ObGyn 4.2 (2012): 110.
Lamont RF and Jayasooriya GS, (2009) 'Progestational Agents for the Prevention of Preterm Birth,' J Perinat Med, 37(1):12-4.
Lee PA et al., (2003) 'International Small for Gestational Age Advisory Board Consensus Development Conference Statement:

(56) References Cited

OTHER PUBLICATIONS

Management of Short Children Born Small for Gestational Age, Apr. 24-Oct. 1, 2001,' Pediatrics, 111(6 Pt 1):1253-61.
LeVine L, (1964) 'Habitual Abortion. A Controlled Study of Progestational Therapy,' West J Surg Obstet Gynecol, 72:30-6.
Lim AC et al., (2007) 'Progesterone for the Prevention of Preterm Birth in Women with Multiple Pregnancies: The AMPHIA Trial,' BMC Pregnancy Childbirth, 7:7.
Makena Product Page. Clinical Advisor. Published online Jun. 30, 2011.
Mason MV et al., (2005) '17 alpha-Hydroxyprogesterone Caproate (17P) Usage in a Medicaid Managed Care Plan and Reduction in Neonatal Intensive Care Unit Days,' Manag Care, 14(10):58-63.
Mason MV et al., (2008) 'Optimizing the Use of 17P in Pregnant Managed Medicaid Members,' Manag Care, 17(1):47-52.
Mason MV et al., (2010) 'Impact of 17P Usage on NICU Admissions in a Managed Medicaid Population—A Five-Year Review,' Manag Care, 19(2):46-52.
McCowan LM et al., (2009) 'Spontaneous Preterm Birth and Small for Gestational Age Infants in Women who Stop Smoking Early in Pregnancy: Prospective Cohort Study,' BMJ, Mar. 26, 2009.
Meis PJ and Aleman A, (2004) 'Progesterone Treatment to Prevent Preterm Birth,' Drugs, 64(21):2463-74.
Meis PJ and the Society for Maternal-Fetal Medicine, (2005) '17 Hydroxyprogesterone for the Prevention of Preterm Delivery,' Obstet Gynecol, 105(5 Pt 1):1128-35.
Meis PJ et al., (2003) 'Prevention of recurrent Preterm Delivery by 17 Alpha-Hydroxyprogesterone Caproate,' N Engl J Med, 348(24):2379-85.
Meis PJ et al., (2005) 'Does Progesterone Treatment Influence Risk Factors for Recurrent Preterm Delivery?,' Obstet Gynecol, 106(3):557-61.
Meis PJ, (2006) 'The Role of 17-a-Hydroxyprogesterone Caproate in the Prevention of Preterm Birth,' Women's Health, 2(6):819-24.
Meyerhoff KH et al., (1962) 'The Use of 17-Alpha-Hydroxyprogesterone Caproate to Maintain Pregnancy,' Curr Ther Res Clin Exp, 4:499-505.
NG SP et al., (2006) 'Hormonal Changes Accompanying Cigarette Smoke-Induced Preterm Births in Mouse Modal,' Exp Biol Med (Maywood), 231(8):1403-9.
Northen AT et al., (2007) 'Follow-up of Children Exposed in Utero to 17 Alpha-Hydroxyprogesterone Caproate Compared with Placebo,' Obstet Gynecol, 110(4):865-72.
O'Brien JM and Lewis DF, (2009) 'Progestins for the Prevention of Spontaneous Preterm Birth: Review and Implications of Recent Studies,' J Reprod Med, 54(2):73-87.
O'Brien JM et al., (2010) 'Uterine Activity in Women Receiving 17 alpha-Hydroxyprogesterone Caproate for the Prevention of Preterm Birth: An Observational Study,' Am J Perinatol, Jul. 30, 2009 (Jul. 30, 2009) (ePub), 27(2):157-62.
O'Brien JM, (2007) 'Progesterone and Preterm Birth,' N Engl J Med, 357(22):2306.
O'Sullivan MD et al., (2010) '17 alpha-Hydroxyprogesterone Caproate Vehicle, Castor Oil, Enhances the Contractile Effect of Oxytocin in Human Myometrium in Pregnancy,' Am J Obstet Gynecol, 202(5):453. e1-4.
Odibo AO et al., (2006) '17Alpha-Hydroxyprogesterone Caproate for the Prevention of Preterm Delivery: A Cost-Effectiveness Analysis,' Obstet Gynecol, 108(3 Pt 1):492-9.
Petrini JR et al., (2005) 'Estimated Effect of 17 Alpha-Hydroxyprogesterone Caproate on Preterm Birth in the United States,' Obstet Gynecol, 105(2):267-72.
Proia, et al. "The effect of angiostatic steroids and β-cyclodextrin tetradecasulfate on corneal neovascularization in the rat." Experimental eye research 57.6 (1993): 693-698.
Rebarber A et al.,(2007) 'Increased Recurrence of Preterm Delivery with Early Cessation of 17-Alpha-Hydroxyprogesterone Caproate,' Am J Obstet Gynecol, 196(3):224.e1-4.

Rebarber A et al.,(2010) 'The Use of 17 Alpha-Hydroxyprogesterone Caproate (17p) in Women with Cervical Cerclage,' Am J Perinatol, 25(5):271-5.
Rebarber A et al.,(2010) 'Using 17 α-Hydroxyprogesterone Caproate to Impact Rates of Recurrent Preterm Delivery in Clinical Practice,' J Matern Fetal Neonatal Med, 23(10):1139-42.
Reifenstein EC Jr, (1957) 'Introduction of Marked as well as Prolonged Biologic Activity by Esterification; 17-alpha-Hydroxyprogesterone Caproate, a Unique Progestational Compound,' Fertil Steril, 8(1):50-79.
Reijinders FJ et al., (1988) 'Endocrine Effects of 17 Alpha-Hydroxyprogesterone Caproate During Early Pregnancy: A Double-Blind Clinical Trial,' Br J Obstet Gynaecol, 95(5):462-8.
Rittenberg C et al., (2007) 'Clinical Characteristics of Women Prescribed 17 alpha-Hydroxyprogesterone Caproate in the Community Setting,' Am J Obstet Gynecol, 197(3):262.e1-4.
Rittenberg C et al., (2008) 'Women Receiving 17-α-Hydroxyprogesterone Caproate Hospitalized for Preterm Labor at Less than 34 Weeks Benefit from Daily Perinatal Nursing Surveillance,' Am J Obstet Gynecol, 199(4):389.e1-4.
Rittenberg C et al., (2009) 'Preterm Birth Prevention by 17 alpha-Hydroxyprogesterone Caproate vs. Daily Nursing Surveillance,' J Reprod Med, 54(2):47-52.
Rode L et al.,(2009) 'Systematic Review of Progesterone for the Prevention of Preterm Birth in Singleton Pregnancies,' Acta Obstet Gynecol Scand, 88(11):1180-9.
Rogers JM et al., (2012) 'SpliceGrapher: Detecting Patterns of Alternative Splicing from RNA-Seq Data in the Context of Gene Models and EST Data,' Genome Biol, 13(1):R4.
Rogers JM, (2009) 'Tobacco and Pregnancy,' Reprod Toxicol, Apr. 9, 2009 (Apr. 9, 2009) (ePub), 28(2):152-60.
Rouse DJ et al., (2007) 'A Trial of 17 Alpha-Hydroxyprogesterone Caproate to Prevent Prematurity in Twins,' N Engl J Med, 357(5):454-61.
Sammour MB et al.,(2005) 'Prevention and Treatment of Pregnancy-Induced Hypertension (Preeclampsia) with Progestogens,' J Steroid Biochem Mol Biol, Oct. 19, 2005 (ePub), 97(5):439-40.
Sanchez-Ramos L et al. (2005) 'Progestational Agents to Prevent Preterm Birth: A Meta-Analysis of Randomized Controlled Trials,' Obstet Gynecol, 105(2):273-9.
Schindler AE, (2004) 'First Trimester Endocrinology: Consequences for Diagnosis and Treatment of Pregnancy Failure,' Gynecol Endocrinol, 18(1):51-7 (Abstract).
Schindler AE, (2005) 'Role of Progestogens for the Prevention of Premature Birth,' J Steroid Biochem Mol Biol, Sep. 29, 2005 (Sep. 29, 2005)(ePub), 97(5):435-8.
Shahin AY et al.,(2009) 'Effect of Oral N-acetyl Cysteine on Recurrent Preterm Labor Following Treatment for Bacterial Vaginosis,' Int J Gynaecol Obstet, Oct. 11, 2008 (ePub), 104(1):44-8.
Shaik IH, (2016), 'Route of Administration and Formulation Dependent Pharmacokinetics of 17-Hydroxyprogesterone Caproate in Rats,' XENOBIOTICA, 46(2): 169-174.
Shearman RP and Garrett WJ, (1963) 'Double-Blind Study of Effect of 17-Hydroxyprogesterone Caproate on Abortion Rate,' Br Med J, 1(5326):292-5.
Sibai B et al., (2005) 'Plasma CRH Measurement at 16 to 20 Weeks' Gestation does not Predict Preterm Delivery in Women at High-Risk for Preterm Delivery,' Am J Obstet Gynecol, 193(3 Pt 2):1181-6.
Simhan HN and Caritis SN, (2007) 'Prevention of Preterm Delivery,' N Engl J Med, 357(5):477-87.
Souka AR et al., (1980) 'Therapeutic Value of Indomethacin in Threatened Abortion,' Prostaglandins, 19(3):457-60.
Spong CY et al., (2005) 'Progesterone for Prevention of Recurrent Preterm Birth: Impact of Gestational Age at Previous Delivery,' Am J Obstet Gynecol, 193(3):1127-31.
Spong CY, (2003) 'Recent Developments in Preventing Recurrent Preterm Birth,' Obstet Gynecol, 101(6):1153-4.
Suchowsky G and Junkmann K, (1958) 'Investigations of the Pregnancy-Maintaining Effect of 17αHydroxyprogesterone Caproate in Spayed Pregnant Rabbits,' Acta Endocrinol—COP, 28:129-31.
Suvonnakote T, (1986) 'Prevention of Pre-Term Labour with Progesterone,' J Med Assoc Thailand, 69(10):537-49.

(56) References Cited

OTHER PUBLICATIONS

Thornton JG, (2007) 'Progesterone and Preterm Labor—Still no Definite Answers,' N Engl J Med, 357(5):499-501.

Tita ATN and Rouse DJ, (2009) 'Progesterone for Preterm Birth Prevention: An Evolving Intervention,' Am J Obstet Gynecol, 200(3):219-24.

Tong VT et al. (2013) 'Trends in Smoking Before, During, and After Pregnancy—Pregnancy Risk Assessment Monitoring System, United States, 40 Sites, 2000-2010,' MMWR Surveill Summ, 62(6):1-19.

Tripathi, et al. "A competitive immunochromatographic strip assay for 17-α-hydroxy progesterone using colloidal gold nanoparticles." Clinica Chimica Acta 413.1 (2012): 262-268.

Uemura, et al. "Effects of 17. ALPHA.-hydroxyprogesterone on luteinizing hormone release in the rat." Endocrinologia japonica 26.2 (1979): 167-173.

Varma TR and Morsman J, (1982), 'Evaluation of the Use of Proluton-Depot (Hydroxyprogesterone Hexanoate) in Early Pregnancy,' Int J Gynaecol Obstet, 20(1):13-7.

Velardo JT, (1958) 'Biological Action of 17 α-Hydroxyprogesterone 17-η-Caproate on the Reproductive Process of the Rat,' Annals NY Acad Sci, 71(5):542-54.

Ventolini G et al., (2008) 'The Impact of Maternal Body Mass on the Effectiveness of 17 alpha-Hydroxyprogesterone Caproate,' J Reprod Med, 53(9):667-71.

Verma, P, (2010), 'Routes of Drug Administration,' IJPSR, 1(1): 45-59.

Vidaeff AC and Ramin SM, (2009) 'Management Strategies for the Prevention of Preterm Birth. Part I: Update on Progesterone Supplementation,' Curr Opin Obstet Gynecol, 21(6):480-4.

Vytiska-Binstorfer E et al., (1986) '[Endocrine Changes Following Progesterone Substitution in Early Pregnancy],' Z Geburtshilfe Perinatol, 190(4):146-8 [Abstract].

Wyatt SN and Rhoads SJ, (2006) 'A Primer on Antenatal Testing for Neonatal Nurses: Part 1. Tests Used to Predict Preterm Labor,' Adv Neonatal Care, 6(4):175-80.

Yemini M et al., (1985) Prevention of Premature Labor by 17 Alpha-Hydroxyprogesterone Caproate, Am J Obstet Gynecol, 151(5):574-7.

Zuidema, J., (1988), 'Release and Absorption Rate Aspects of Intramuscularly Injected Pharmaceuticals,' Int. J. Pharm., 47:1-12.

U.S. Appl. No. 12/971,900, Methods for Reducing the Occurrence of Preterm Delivery and Other Pregnancy-Related Conditions, filed Dec. 17, 2010, Abandoned.

U.S. Appl. No. 15/147,500, Methods for Reducing the Occurrence of Preterm Delivery and Other Pregnancy-Related Conditions, filed May 5, 2016, Pending.

U.S. Appl. No. 15/143,867, Methods of Reducing Risks of Preterm Birth, filed May 2, 2016, Abandoned.

U.S. Appl. No. 15/373,262, Methods of Reducing Risks of Preterm Birth, filed Dec. 8, 2016, Granted.

U.S. Appl. No. 15/709,941, Methods of Reducing Risks of Preterm Birth, filed Sep. 20, 2017, Pending.

PCT/US17/32816, Polymeric Extended Release Compositions of Hydroxyprogesterone Caproate and Methods of Using Same, filed Jun. 16, 2017, Pending.

* cited by examiner

CRYSTALLINE AND AMORPHOUS FORMS OF 17-ALPHA-HYDROXYPROGESTERONE CAPROATE

CROSS-REFERENCE TO RELATED APPLICATIONS

This application is the national stage application of International (PCT) Patent Application Serial No. PCT/US2016/054446, filed Sep. 29, 2016, and published under PCT Article 21(2) in English, which claims the benefit of and priority to U.S. Ser. No. 62/234,280 filed Sep. 29, 2015, the entire disclosure of each of which is incorporated by reference in its entirety herein.

BACKGROUND

Preterm delivery and other pregnancy-related conditions such as the delivery of low birth weight neonates and/or small for gestational age neonates have serious health, societal, and economic costs. For example, preterm delivery and the delivery of low birth weight neonates and/or small for gestational age neonates can lead to neonatal morbidity, longer stays in the neonatal intensive care unit, and a higher risk of long term morbidities including, for example, cerebral palsy, mental retardation, and learning disabilities.

Administration of steroids such as 17-α-hydroxyprogesterone caproate ("17-HPC" or "HPC") has been used to reduce the risk of, e.g., preterm birth. HPC has the structure:

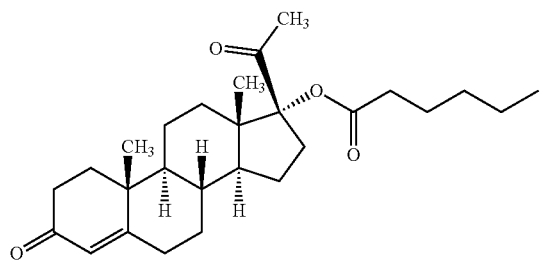

Polymorphism is the ability of a substance to crystallize in more than one crystal lattice arrangement. Crystallization, or polymorphism, can influence many aspects of solid state properties of a drug substance. A crystalline substance may differ considerably from an amorphous form, and different crystal modifications of a substance may differ considerably from one another in many respects including solubility, dissolution rate and/or bioavailability. Generally, it is difficult to predict whether or not a given compound will form various crystalline solid state forms. It is even more difficult to predict the physical properties of these crystalline solid state forms. Further, it can be advantageous to have a crystalline form of a therapeutic agent for certain formulations.

SUMMARY

This disclosure is generally directed to crystalline and amorphous forms of HPC. For example, provided herein in an embodiment is a crystalline form of HPC characterized by a powder X-ray diffraction pattern having a characteristic peak in degrees 2θ at about 18.3, for example, characterized by a powder X-ray diffraction pattern having characteristic peaks in degrees 2θ at about 9.6, 12.2, and 18.3 (Form B). In some embodiments, a disclosed crystalline form has a differential scanning calorimetry endothermic peak at about 100-105° C. Contemplated herein is a drug substance comprising at least a detectable amount of a disclosed crystalline form. For example, provided herein is a composition comprising at least about 10% Form B HPC or e.g., about 10% to at least about 50% a Form B HPC by weight.

Also provided herein is a substantially amorphous form of HPC. For example, provided herein is a drug substance comprising at least about 10% amorphous HPC by weight, or e.g., about 50% amorphous HPC by weight. Contemplated amorphous compositions may further comprising a crystalline form of HPC characterized by a powder X-ray diffraction pattern having a characteristic peak in degrees 2θ at about 18.3, and/or a crystalline form of HPC characterized by a powder X-ray diffraction pattern having a characteristic peak in degrees 2θ at about 7.3.

Pharmaceutical compositions are also provided that include a disclosed crystalline and/or amorphous forms. Also provided herein are methods of making and using the disclosed crystalline and/or amorphous forms

DETAILED DESCRIPTION

Figure 1:
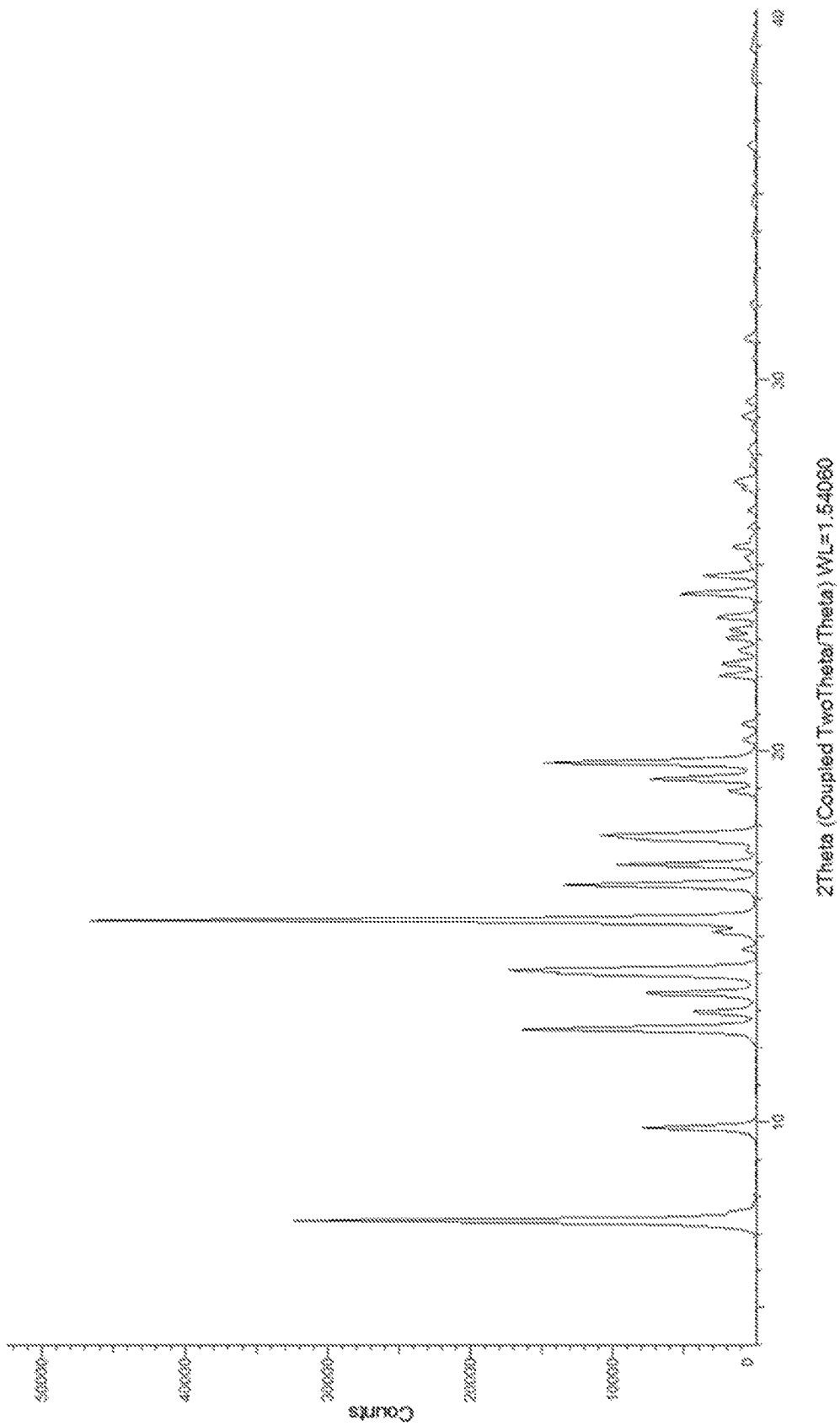
FIG. 1 depicts the X-ray diffraction pattern of Form A prepared by Example 1.

At least in part, this disclosure is directed to crystalline forms of HPC. The disclosure also provides for a pharmaceutical composition comprising crystalline HPC and a pharmaceutically acceptable carrier. The term "crystalline form" refers to a crystal form or modification that can be characterized by analytical methods such as, e.g., X-ray powder diffraction. For example, provided herein is a drug substance comprising at least a detectable amount of a disclosed crystalline form of HPC.

In an embodiment, provided herein is a crystalline form of HPC characterized by a powder X-ray diffraction pattern having a characteristic peak in degrees 2θ at about 15.4 (referred to herein as "Form A"). The term "about" in the context of peaks at degrees 2θ means that there is an uncertainty in the measurements of the 2θ of ±0.5 (expressed in 2θ) or that there is an uncertainty in the measurements of the 2θ of ±0.2 (expressed in 2θ).

In one embodiment, the crystalline Form A of HPC is characterized by a powder X-ray diffraction pattern that has a characteristic peak in degrees 2θ at about 7.3, is characterized by a powder X-ray diffraction pattern that has a characteristic peak in degrees 2θ at about 9.8, is characterized by a powder X-ray diffraction pattern that has a characteristic peak in degrees 2θ at about 12.5, is characterized by a powder X-ray diffraction pattern that has a characteristic peak in degrees 2θ at about 13.0, is characterized by a powder X-ray diffraction pattern that has a characteristic peak in degrees 2θ at about 13.5, is characterized by a powder X-ray diffraction pattern that has a characteristic peak in degrees 2θ at about 14.0, is characterized by a powder X-ray diffraction pattern that has a characteristic peak in degrees 2θ at about 14.1, is characterized by a powder X-ray diffraction pattern that has a characteristic peak in degrees 2θ at about 16.4, is characterized by a powder X-ray diffraction pattern that has a characteristic peak in degrees 2θ at about 16.9, is characterized by a powder X-ray diffraction pattern that has a characteristic peak in degrees 2θ at about 17.7, is characterized by a powder X-ray diffraction pattern that has a characteristic peak in degrees 2θ at about 19.2, is characterized by a powder X-ray diffraction pattern that has a characteristic peak in degrees 2θ at about 19.7, and/or is characterized by a powder X-ray diffraction pattern that has a characteristic peak in degrees 2θ at about 24.2. In another embodiment, crystalline Form A is characterized by a powder X-ray diffraction pattern having at least one or more characteristic peaks in degrees 2θ at about 7.3, 14.1, and 15.4. In a further embodiment, the crystalline form is characterized by a powder X-ray diffraction pattern having at least one or more characteristic peaks in degrees 2θ at about 7.3, 12.5, 14.0, 14.1, 15.4, 16.4, and 19.7. In yet another embodiment, the crystalline form is characterized by a powder X-ray diffraction pattern having at least one or more characteristic peaks in degrees 2θ at about 7.3, 9.8, 12.5, 14.0, 14.1, 15.4, 16.4, 16.9, 17.7, and 19.7. In some embodiments, the crystalline form is characterized by a powder X-ray diffraction pattern having at least one or more characteristic peaks in degrees 2θ at about 7.3, 9.8, 12.5, 13.0, 13.5, 14.0, 14.1, 15.4, 16.4, 16.9, 17.7, 19.2, 19.7, and 24.2. For example, a contemplated crystalline form has a powder X-ray diffraction pattern shown in FIG. 1. In one embodiment, the powder X-ray diffraction pattern of the crystalline form was obtained using Cu Kα radiation. In a further example, contemplated crystalline Form A has a $^1$H NMR spectrum substantially in accordance with the pattern shown in FIG. 3, wherein the crystalline form is in solution.

The contemplated crystalline form of Form A HPC may be characterized by a differential scanning calorimetry profile with an endothermic peak from about 120° C. to about 124° C. Form A, for example, is characterized by the differential scanning calorimetry profile shown in FIG. 2. Form A, for example, has a solubility in methanol of about 142 mg/mL at 25° C., a solubility in ethanol of about 118 mg/mL at 25° C., a solubility in isopropanol of about 91 mg/mL at 25° C., and a solubility in ethyl acetate of about 419 mg/mL at 25° C.

Also provided herein is a process for preparing a crystalline form of HPC, Form A, comprising: a) preparing a solution of HPC in a heated solvent. Such solvents contemplated may include e.g., an alcohol; b) slowly evaporating the solution to dryness; and c) isolating the crystalline Form A of HPC. In an exemplary embodiment, the alcohol is methanol. Other contemplated solvents include alcohols such as ethanol and/or isopropanol, acetone, acetonitrile, cyclohexane, ethyl acetate, n-heptane, methyl ethyl ketone, methyl isobutyl ketone, tetrahydrofuran, toluene, and/or a combination of two or more thereof. In some embodiments, a heated solvent comprises heating a solvent to about 40° C. to about 60° C., e.g., to about 50° C.

In another embodiment, a different crystalline form of HPC characterized by a powder X-ray diffraction pattern having a characteristic peak in degrees 2θ at about 18.3 (referred to herein as "Form B"), is provided.

In one embodiment, the crystalline Form B of HPC is characterized by a powder X-ray diffraction pattern that has a characteristic peak in degrees 2θ at about 3.9, is characterized by a powder X-ray diffraction pattern that has a characteristic peak in degrees 2θ at about 12.2, is characterized by a powder X-ray diffraction pattern that has a characteristic peak in degrees 2θ at about 13.0, is characterized by a powder X-ray diffraction pattern that has a characteristic peak in degrees 2θ at about 13.9, is characterized by a powder X-ray diffraction pattern that has a characteristic peak in degrees 2θ at about 14.8, is characterized by a powder X-ray diffraction pattern that has a characteristic peak in degrees 2θ at about 15.4, is characterized by a powder X-ray diffraction pattern that has a characteristic peak in degrees 2θ at about 16.5, is characterized by a powder X-ray diffraction pattern that has a characteristic peak in degrees 2θ at about 19.2, is characterized by a powder X-ray diffraction pattern that has a characteristic peak in degrees 2θ at about 21.0, is characterized by a powder X-ray diffraction pattern that has a characteristic peak in degrees 2θ at about 24.5, is characterized by a powder X-ray diffraction pattern that has a characteristic peak in degrees 2θ at about 24.9, and/or is characterized by a powder X-ray diffraction pattern that has a characteristic peak in degrees 2θ at about 30.7. In another embodiment, crystalline Form B is characterized by a powder X-ray diffraction pattern having at least one or more characteristic peaks in degrees 2θ at about 9.6, 12.2, and 18.3. In a further embodiment, the crystalline form is characterized by a powder X-ray diffraction pattern having at least one or more characteristic peaks in degrees 2θ at about 9.6, 12.2, 13.9, 14.8, 15.4, 18.3, and 19.2. In yet another embodiment, the crystalline form is characterized by a powder X-ray diffraction pattern having at least one or more characteristic peaks in degrees 2θ at about 3.9, 9.6, 12.2, 13.0, 13.9, 14.8, 15.4, 18.3, 19.2, and 30.7. In some embodiments, the crystalline form is characterized by a powder X-ray diffraction pattern having at least one or more characteristic peaks in degrees 2θ at about 3.9, 9.6, 12.2, 13.0, 13.9, 14.8, 15.4, 16.5, 18.3, 19.2, 21.0, 24.5, 24.9, and 30.7. For example, contemplated crystalline Form B has a powder X-ray diffraction pattern shown in FIG. 4. In one embodiment, the powder X-ray diffraction pattern of crystalline Form B was obtained using Cu Kα radiation. In a further example, contemplated crystalline Form B has a $^1$H NMR spectrum substantially in accordance with the pattern shown in FIG. 6, wherein the crystalline form is in solution.

The contemplated crystalline form of Form B HPC may be characterized by a melting point of about 104° C., for example, and/or may be characterized by a differential scanning calorimetry profile with an endothermic peak from about 100° C. to about 105° C. Form B, for example, is characterized by the differential scanning calorimetry profile shown in FIG. 5. One of skill in the art understands that, certain embodiments, e.g., when Form B forms part of a solid formulation (e.g., including fillers and/or other excipients), the endothermic peak may be suppressed to lower values.

Also provided herein is a process for preparing a crystalline form of HPC, Form B, comprising: a) adding HPC to a solvent that is saturated with HPC. Such solvents contemplated may include e.g., an ester; b) stirring the resulting slurry for extended time at a temperature of about 20-22° C.; and c) isolating crystalline Form B of HPC. In an exemplary embodiment, the ester is ethyl acetate. Other contemplated solvents include alcohols such as methanol and/or isopropanol, acetone, acetonitrile, cyclohexane, n-heptane, methyl ethyl ketone, methyl isobutyl ketone, tetrahydrofuran, toluene, and/or a combination of two or more thereof. In some embodiments, stirring the slurry comprises stirring for at least one day, e.g., about 8 to 24 hours, or about 1 to 2 days. In some embodiments, a provided process further comprises filtering the slurry.

The disclosure also provides for amorphous forms of HPC, for example, provides, in some embodiments, a drug substance having substantially amorphous HPC. In another embodiment, a drug substance is provided that comprises at least about 10% amorphous HPC by weight, about 10-30% by weight (e.g., based on total weight of HPC). Also provided is a drug substance comprising at least about 50% amorphous HPC by weight.

For example, provided herein is a composition or drug substance comprising a disclosed amorphous form of HPC and further comprising a crystalline form of HPC characterized by a powder X-ray diffraction pattern having a characteristic peak in degrees 2θ at about 18.3 (e.g., Form B). In another embodiment, provided herein is a composition or drug substance comprising a disclosed amorphous form of HPC and further comprising a crystalline form of HPC characterized by a powder X-ray diffraction pattern having a characteristic peak in degrees 2θ at about 7.3.

Also provided herein is a method for analyzing a HPC sample for the presence of crystalline Form B, wherein Form B is characterized by a powder X-ray diffraction pattern having characteristic peaks in degrees 2θ at about 9.6, 12.2, and 18.3, comprising: providing a HPC sample (e.g., where the HPC sample is a composition comprising HPC and an excipient); using an analytic process to determine the presence of Form B; and making a determination about the HPC sample based upon a comparision of the determination of the presence of Form B to a standard for HPC, wherein the determination based on the comparision to the standard relates to the quality of the sample, and thereby analyzing the HPC sample. Contemplated analytic processes may include differential scanning calorimetry, X-ray powder diffraction (XRPD), solid state NMR, FTIR spectroscopy, near infrared (NIR) spectroscopy, Raman spectroscopy and/or a dissolution assay. Using an analytic process may include for example, determining an endothermic peak at about 100-105° C. The standard for HPC can include a melting point of about 120 to about 124° C., e.g., melting point of about 119 to about 121° C. and/or may include a standard for HPC that includes an amount of free n-caproic acid of less than about 0.58%.

Compositions

Another aspect of the disclosure provides pharmaceutical compositions comprising crystalline and/or amorphous form of HPC as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

While many steroids are produced as injectable or oral suspension dosage forms due to their low solubility in aqueous formulation solvents, in some embodiments, a disclosed formulation (e.g. a suspension formulation that includes Form B as disclosed herein), may include higher doses of active, and/or may avoid oily excipients (e.g., castor oil) that may increase irritation upon injection.

Exemplary pharmaceutical compositions may be used in the form of a pharmaceutical preparation, for example, in solid, semisolid or liquid form, which contains one or more of crystalline and/or amorphous form of HPC as disclosed herein, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient, e.g., crystalline and/or amorphous form of HPC as disclosed herein, may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, water solubilizers and/or absorbance enhancers, such a talc, calcium stearate, capric acid magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository (or e.g. IUD or vaginal ring), which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions that include crystalline and/or amorphous form of HPC as disclosed herein may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols.

In another aspect, provided herein are enteral pharmaceutical formulations including a crystalline and/or amorphous form of HPC as disclosed herein and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e. g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present invention.

Also provided herein in an embodiment are extended release pharmaceutical formulations and compositions that include a crystalline and/or amorphous form of HPC as disclosed herein. Contemplated compositions include implants, devices, nanoparticles, microparticles, liposomes, and self-emulsifying drug delivery systems. For example compositions may include biodegradable and/or biocompatible polymer such as poly(glycolide-co-lactide) (PLGA), polylactic acid (PLA), polyglycolic acid (PGA), polyethylene glycol (PEG), and/or polycaprolactone (PCL). For example, comtemplated herein are implants or devices such as an IUD, vaginal ring, or stent, or a pellet type implant and a biodegradable and/or biocompatible polymer. Also contemplated herein are microparticles or nanoparticles having a crystalline and/or amorphous form of HPC as disclosed herein and an biodegradable and/or biocompatible polymer such as poly(glycolide-co-lactide) (PLGA), polylactic acid (PLA), polyglycolic acid (PGA), polyethylene glycol (PEG), and/or polycaprolactone (PCL).

Pharmaceutical compositions contemplated herein may include about 100 milligrams (mg) to about 3000 mg of a disclosed crystalline and/or amorphous form of HPC, e.g., Form A or Form B, or a mixture thereof. For example, contemplated methods include administering a pharmaceutical composition that includes a disclosed crystalline and/or amorphous form and e.g., an oil, e.g. castor oil, on a once-monthly basis. Such pharmaceutical compositions may include at least about 50 mg, at least about 100 mg, at least about 200 mg, at least about 300 mg, at least about 400 mg, at least about 500 mg, at least about 750 mg, at least about 1000 mg, at least about 1500 mg, at least about 2000 mg, or at least about 2500 mg of a disclosed crystalline form, e.g., Form A or Form B (or a mixture thereof). In accordance with this and various other embodiments, such pharmaceutical compositions may further include less than about 3000 mg, less than about 2500 mg, less than about 2000 mg, less than about 1500 mg, less than about 1000 mg, less than about 500 mg, or less than about 250 mg of a disclosed crystalline form and/or amorphous form. In certain embodiments, contemplated compositions can include for example about 5% form A and about 95% Form B, by weight of HPC present, e.g., about 0 to about 10% by weight Form A and about 10 to about 90% or more Form B by weight of HPC present.

For example, a pharmaceutical composition is provided that includes a disclosed crystalline and/or amorphous form of HPC, for example, provided herein is a tablet, capsule, chewable form, sublingual form, lozenge, solid state dispersion, suspension, implant (e.g., biodegradable polymeric implant), IUD, and/or extended release formulation (e.g., a composition that includes microparticle or nanoparticles) that include a disclosed crystalline and/or amorphous form. Such pharmaceutical compositions/dosage forms may include at least about 50 mg, at least about 75 mg, at least about 100 mg, at least about 150 mg, at least about 200 mg, at least about 250 mg, at least about 500 mg, at least about 750 mg, or at least about 1000 mg of a disclosed crystalline and/or amorphous form of HPC. In accordance with this and various other embodiments, such pharmaceutical compositions may further include less than about 1600 mg, less than about 1500 mg, less than about 1250 mg, less than about 1000 mg, less than about 800 mg, less than about 500 mg, or less than about 350 mg of a disclosed crystalline form of HPC. For example, a contemplated method includes subcutaneously administering a pharmaceutical composition comprising a disclosed crystalline form of HPC to a pregnant human female subject on a once-weekly basis, said pharmaceutical composition suitably including from about 50 mg to about 1600 mg, from about 100 mg to about 800 mg, or about 250 mg of a disclosed crystalline form.

For example, contemplated methods may include subcutaneously administering a dose of a disclosed pharmaceutically acceptable viscous non-aqueous liquid formulation having about 187 mg to about 400 mg of a crystalline form of HPC, where the dose has a volume of about 0.70 mL to about 2 mL, about 1.0 mL, about 1.1 mL, about 1.2 mL, about 1.3 mL, or about 1.4 mL, e.g., a volume of about 1.1 mL to about 1.4 mL, about 1.3 mL to about 1.4 mL, about 1.1 mL to about 1.6 mL, or about 1.4 mL.

Contemplated herein are methods that include subcutaneous administration of about 1.1 mL to about 1.4 mL of a pharmaceutically acceptable viscous non-aqueous liquid formulation having a concentration of about 250 mg/mL of HPC.

In still another embodiment, contemplated methods include subcutaneously or intravenously administering to a pregnant human female subject a first pharmaceutical composition comprising a disclosed crystalline form on a once- or twice-weekly basis for 1 to 2 weeks, followed by a second pharmaceutical composition comprising a crystalline form on a once-weekly basis for the remainder of the treatment. In this embodiment, it is contemplated that both the first and second pharmaceutical compositions will include HPC and a pharmaceutically acceptable viscous non-aqueous liquid carrier, e.g., that includes an oil (such as castor oil), and that the first pharmaceutical composition will include an equal or greater amount of HPC than the second pharmaceutical composition. Said first pharmaceutical compositions may include at least about 25 mg, at least about 50 mg, at least about 100 mg, at least about 250 mg, at least about 500 mg, at least about 750 mg, at least about 1000 mg, or at least about 1500 mg of HPC. Said second pharmaceutical compositions may include at least about 25 mg, at least about 50 mg, at least about 100 mg, at least about 250 mg, at least about 500 mg, at least about 750 mg, at least about 1000 mg, at least about 1500 mg of HPC, for example, wherein the first pharmaceutical composition contains an equal or greater amount of HPC than the second pharmaceutical composition. In accordance with this and various other embodiments, said first pharmaceutical composition may include less than about 1600 mg, less than about less than about 1250 mg, less than about 1000 mg, less than about 800 mg, less than about 500 mg, or less than about 350 mg of a disclosed crystalline compound. Similarly, said second pharmaceutical composition may include less than about 1600 mg, less than about 1250 mg, less than about 1000 mg, less than about 800 mg, less than about 500 mg, or less than about 350 mg of a disclosed crystalline form, wherein the first pharmaceutical composition contains an equal or greater amount of HPC than the second pharmaceutical composition. For example, a contemplated method includes subcutaneously administering to a pregnant human female subject, a first pharmaceutical composition comprising a disclosed crystalline form, once- or twice-weekly for one to two weeks, followed by a second pharmaceutical composition comprising a disclosed crystalline form once-weekly for the remainder of the treatment. The first pharmaceutical composition may include from about 50 mg to about 1600 mg, from about 100 mg to about 800 mg, or about 250 mg of a disclosed crystalline form. The second pharmaceutical composition may include from about 50 mg to about 1600 mg, from about 100 mg to about 800 mg, or about 250 mg of a crystalline form of HPC wherein the first pharmaceutical composition contains an equal or greater amount of HPC than the second pharmaceutical composition.

Generally, disclosed methods include administration of a pharmaceutically acceptable composition that includes a disclosed amorphous and/or crystalline HPC that additionally contains one or more pharmaceutically acceptable excipients. For example, provided herein is a pharmaceutically acceptable viscous non-aqueous liquid formulation that includes a detectable amount of a disclosed crystalline form. For example, a contemplated pharmaceutical composition may contain one or more diluents, one or more carriers, one or more solvents, one or more viscosity enhancement agents, one or more buffers, one or more preservatives, one or more dyes, one or more absorption enhancers, and/or one or more biodegradable polymers (e.g., a nanoparticle composition having nanoparticles that include a disclosed amorphous and/or crystalline HPC and a biodegradable polymer, e.g. a coated nanoparticle).

Methods

In certain embodiments, the disclosure provides a method of reducing the risk of preterm birth in a pregnant human female patient in need thereof by administering an effective amount of a disclosed crystalline and/or amorphous compound (HPC), e.g., Form A or Form B (or a mixture thereof), or a composition having Form A or Form B as contemplated herein. Also provided herein are methods for reducing the risk of preterm birth in a pregnant human female patient in need thereof, comprising administering a disclosed crystalline compound.

For example, described herein are methods for reducing the occurrence of preterm delivery and/or reducing the occurrence of other pregnancy-related conditions such as delivery of low birth weight neonates, delivery of small for gestational age neonates, pregnancy-related complications, fetal mortality, neonatal morbidity, neonatal mortality, infant morbidity, infant mortality, and childhood developmental delays in a human female patient (e.g., a human female patient pregnant with a singleton or with multiple fetuses). For example, methods disclosed herein are effective for reducing the occurrence of preterm delivery in a pregnant human female subject at risk for preterm delivery. Risk factors for preterm delivery and/or other pregnancy-related conditions include previous preterm delivery, exposure to tobacco smoke, exposure to tobacco smoke residue, use of smokeless tobacco, substance use or abuse or dependence, alcohol use or abuse or dependence, stress, anxiety, depression, poor nutritional status, insufficient weight gain during pregnancy, advanced maternal age, low socio-economic status, and combinations thereof.

Advantageously, the methods disclosed herein include subcutaneous (SQ), intramuscular, oral, rectal or vaginal administration of a composition comprising a disclosed crystalline form of HPC and can provide effective treatment to pregnant human females at risk of e.g. a preterm delivery. For example, provided are methods of treating reducing the occurrence of preterm delivery and/or reducing the occurrence of other pregnancy-related condition comprising administering a disclosed crystalline and/or amorphous form of HPC comprising opthalmically, vaginally, rectally, topically, parenterally (e.g., subcutaneously, intravenously or intramuscularly), transdermally (or intradermally), buccally, orally (e.g., in the form of a capsule, tablet, chewable, sublingual, lozenge, solid state dispersion, suspension, or the like), intranasally, by inhalation, optically, sublingually or by implant.

In particular, in certain embodiments, the disclosure provides a method of treating one or more of the above medical indications comprising administering to a subject in need thereof a therapeutically effective amount of a crystalline compound described herein. In certain other embodiments, a method of reducing the risk of preterm birth in a patient in need thereof is provided, comprising subcutaneously or intramuscularly administering a composition comprising a disclosed crystalline form of HPC.

For example, contemplated methods may include administration of a viscous non-aqueous liquid formulation comprising a disclosed crystalline or amorphous form; for example a viscous non-aqueous liquid formulation comprising a disclosed crystalline form and a pharmaceutically acceptable oil (e.g., castor oil and/or benzyl benzoate). Contemplated methods include subcutaneously administering a pharmaceutical composition to a pregnant female subject, said pharmaceutical composition comprising at least a detectable amount of the crystalline form and a viscous oil e.g. with a 250-1000 cP at 25° C. In an embodiment, methods disclosed herein include subcutaneous administration of an essentially preservative free pharmaceutical composition that includes a crystalline form of HPC and castor oil. For example, methods disclosed herein include subcutaneous administration of a pharmaceutical composition that consists essentially of a crystalline and or amorphous form of HPC as disclosed herein, castor oil, and benzyl benzoate In an embodiment, a method of treating a pregnant human female patient in need of reducing the risk of preterm birth is provided comprising subcutaneously administering a formulation comprising a disclosed crystalline form of HPC and a mixture of non-aqueous solvents such as benzyl benzoate and castor oil.

For example, provided herein are methods comprising administering a disclosed pharmaceutical composition having a disclosed crystalline and/or amorphous form is administered at an interval of once a week or exceeding once per week, for example, administered about weekly beginning about 16 weeks of gestation (e.g., beginning between about 16 weeks, zero days and about 20 weeks, six days of gestation), until about 37 weeks of gestation or until delivery. For example, a contemplated pharmaceutical composition may be administered once every other week, once monthly, once every two months, or once every three months. In various other embodiments, the pharmaceutical composition is administered about once weekly, or at an interval of less than one week (e.g., daily or every other day).

In one embodiment, contemplated methods include orally, subcutaneously or intramuscularly administering a pharmaceutical composition comprising a disclosed crystalline and/or amorphous form form of HPC or composition thereof to a pregnant human female subject on a weekly basis, or more than once a week basis, e.g. subcutaneously administering HPC every 7 days, every 8 days, every 9 days, every 10 days, every 11 days, every 12 days, every 13 days, or every other week. For example, contemplated methods include administering a disclosed pharmaceutical composition that includes a disclosed crystalline form of HPC and/or amorphous form and an oil, e.g. castor oil, on an about weekly, or a more-than-once-a-week basis.

The crystalline and/or amorphous compounds disclosed herein can be used as a medicament or pharmaceutically acceptable composition, e.g., in the form of pharmaceutical preparations for enteral, parenteral, or topical administration, and the contemplated methods disclosed herein may include administering enterally, parenterally, or topically a disclosed crystalline compound, or a composition comprising or formed from such a disclosed crystalline compounds. For example, a disclosed crystalline form, e.g., Form A or Form B, (or a mixture thereof) may be capable of controlling one or more pharmacokinetic properties (e.g., a longer or shorter release profile) when administered by a certain route (e.g., subcutaneous) or in a certain formulation, as compared to a different route (e.g., intravenous) or other formulation e.g., a formulation having the amorphous form. In one embodiment, a disclosed crystalline form, e.g., Form A or Form B, may afford substantial reproducibility from one formulation to another.

Kits

In one embodiment, a kit for treating obesity or other contemplated disorder is provided. For example, a disclosed kit comprises a disclosed crystalline and/or amorphous form of HPC, e.g., a crystalline form of HPC, e.g., Form A or Form B, or a mixture thereof for example, disposed in an e.g., first container. In some embodiments, a kit may further include a pharmaceutically acceptable excipient, disposed in e.g a second container. Such contemplated kits may include written instructions describing preparation of a pharmaceutical composition suitable for administration to a patient from the crystalline form. For example, the written instructions may describe preparing a pharmaceutically acceptable form for patient administration by, e.g., mixing an excipient and a crystalline compound disclosed herein. Disclosed kits may further comprise written instructions describing how to administer the resulting composition to the patient.

EXAMPLES

The compounds described herein can be prepared in a number of ways based on the teachings contained herein and synthetic procedures known in the art. The following non-limiting examples illustrate the disclosed inventions.

Example 1

Crystalline, Form A material of HPC was prepared as follows:

Approximately 142 mg of HPC was dissolved in methanol at 50° C. The solution was allowed to slowly evaporate to dryness to obtain a quantitative amount of solid Form A characterized by X-ray powder diffraction (XRPD).

XRPD patterns were obtained using a Bruker D8 Advance X-Ray Diffractometer equipped with a Cu Kα radiation source (λ=1.54° A) in locked/coupled mode. A 9-position sample changer and LYNXEYE high speed detector were used. Samples were placed on zero-background, silicon plate holders. The step was 0.05°. Count times were 1.3 second per step.

The XRPD of HPC Form A is shown in FIG. 1. Characteristic peaks include one or more of the peaks shown in Table 1, below.

TABLE 1

| Angle, 2 θ | d spacing, °A | Relative intensity, % |
| --- | --- | --- |
| 7.34 | 12.02681 | 70 |
| 9.84 | 8.98498 | 16.7 |
| 12.49 | 7.08102 | 34.3 |
| 12.97 | 6.82277 | 9.02 |
| 13.46 | 6.57181 | 15.7 |
| 14.05 | 6.29968 | 31.6 |
| 14.09 | 6.2818 | 36.2 |
| 15.13 | 5.85074 | 6.3 |
| 15.43 | 5.73699 | 100 |
| 16.39 | 5.40578 | 29.1 |
| 16.93 | 5.23221 | 21.4 |
| 17.68 | 5.01303 | 20.9 |
| 19.24 | 4.60956 | 15.8 |
| 19.68 | 4.50777 | 31.1 |
| 22.03 | 4.03248 | 5.4 |
| 23.60 | 3.76693 | 5.6 |
| 24.23 | 3.67026 | 11.3 |
| 24.72 | 3.598 | 7.9 |

Figure 2:
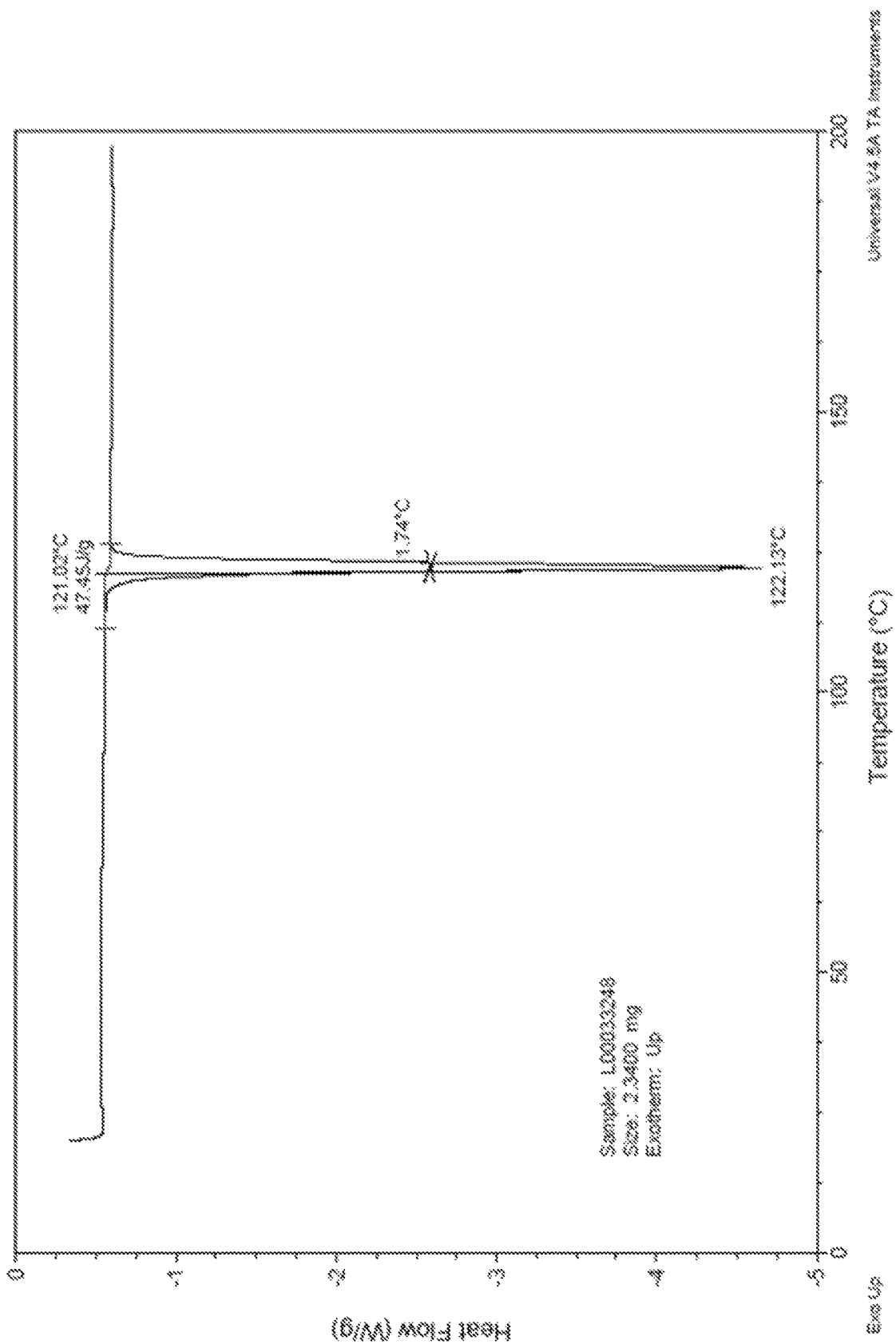
FIG. 2 depicts the characterization of Form A, prepared by Example 1, by differential scanning calorimetry (DSC).

DSC data were collected using a TA Instruments Q1000 DSC equipped with auto-sampler. Typically, samples (~2-7 mg) were placed in hermetic alodined aluminum sample pans and scanned from 30° to 180° C. at a rate of 10° C./min under a nitrogen purge of 50 mL/min. Results are depicted in FIG. 2. All endotherms present in the DSC traces point in the downward direction.

Figure 3:
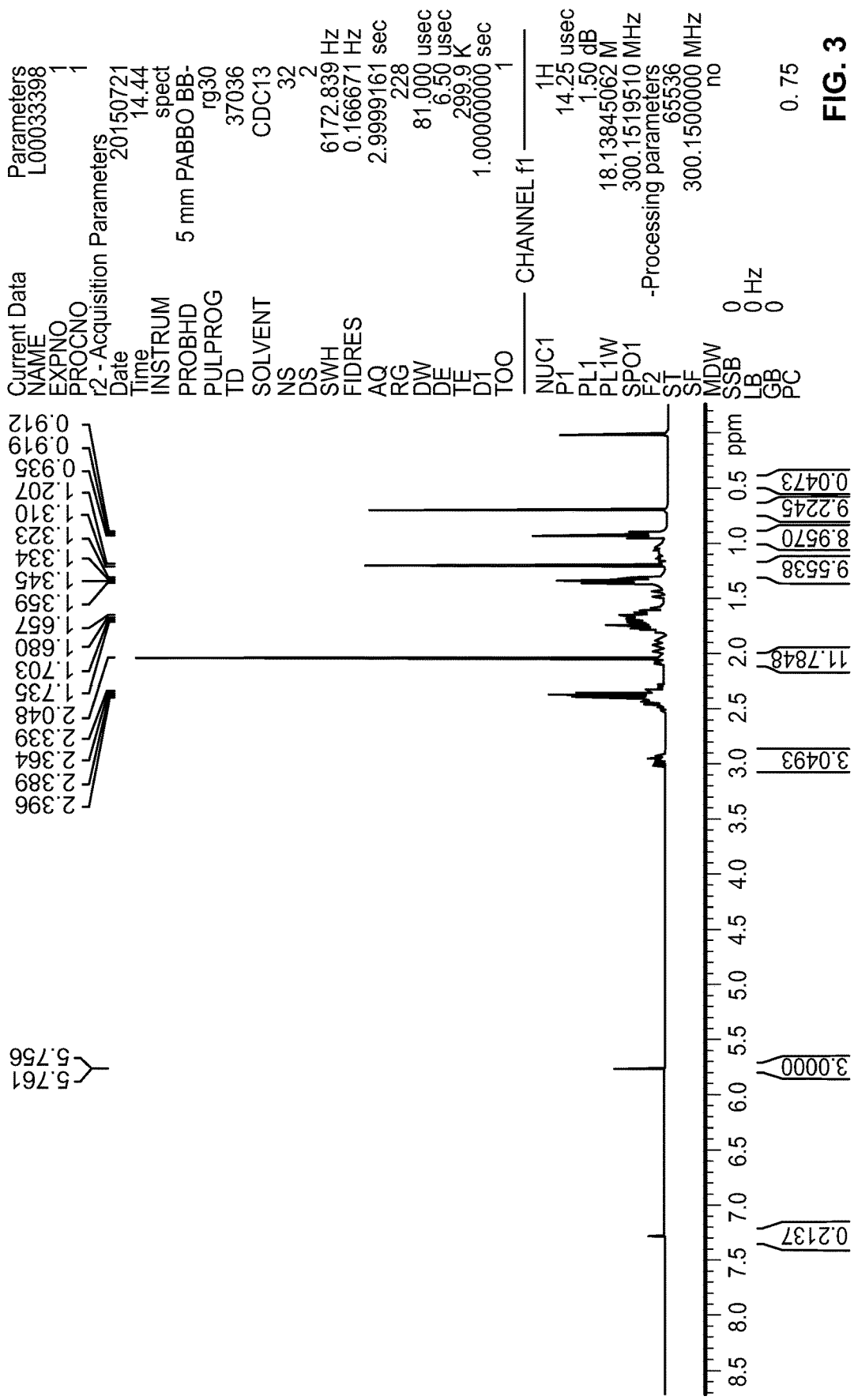
FIG. 3 depicts the $^1$H NMR spectrum of the dissolved crystal of Form A prepared by Example 1.

$^1$H NMR was performed on a Bruker NMR spectrometer. Samples were prepared in deuterated chloroform. The spectrum is depicted in FIG. 3.

Example 2

Crystalline, Form B material of HPC was prepared as follows:

Approximately 1.4 g of Form A material of HPC was added to a solution of ethyl acetate already saturated with HPC. The resulting slurry was stirred for an extended time of at least one day at a temperature of about 20-22° C. The solid was filtered and dried under vacuum at room temperature to yield crystalline material of Form B characterized by XRPD.

X-ray powder diffraction (XRPD) patterns were obtained using a Bruker D8 Advance X-Ray Diffractometer equipped with a Cu Kα radiation source (λ=1.54° A) in locked/coupled mode. A 9-position sample changer and LYNXEYE high speed detector were used. Samples were placed on zero-background, silicon plate holders. The step was 0.05°. Count times were 1.3 second per step.

Figure 4:
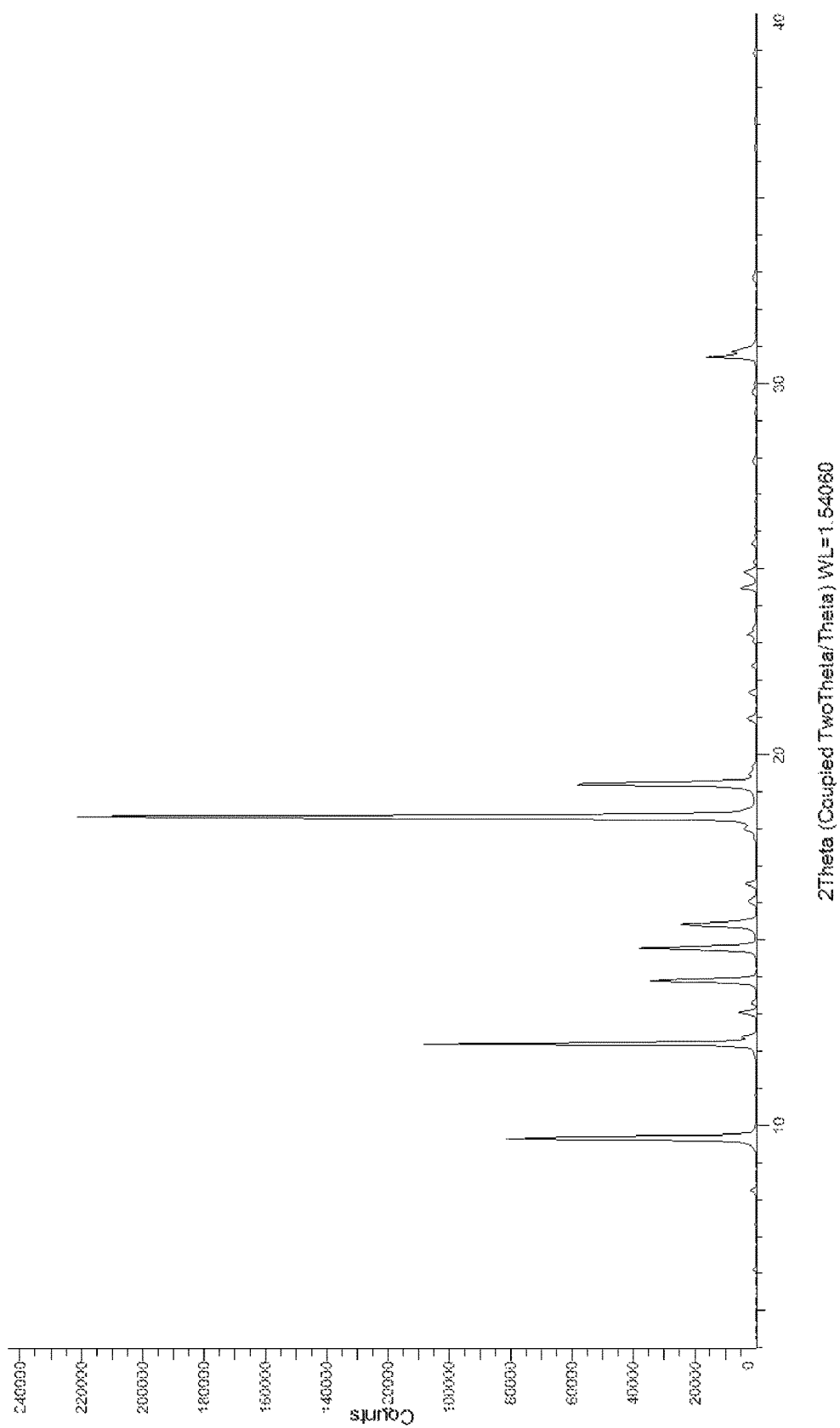
FIG. 4 depicts the X-ray diffraction pattern of Form B prepared by Example 2.

The XRPD of HPC Form B is shown in FIG. 4. Characteristic peaks include one or more of the peaks shown in Table 2, below.

TABLE 2

| Angle, 2 θ | d spacing, °A | Relative intensity, % |
| --- | --- | --- |
| 6.05 | 14.60083 | 1 |
| 8.24 | 10.71775 | 1 |
| 9.65 | 9.15948 | 36.8 |
| 12.19 | 7.25756 | 48.7 |
| 13.04 | 6.78543 | 2.6 |
| 13.89 | 6.3692 | 15.6 |
| 14.79 | 5.98661 | 17.6 |
| 15.43 | 5.73953 | 10.9 |
| 16.09 | 5.50421 | 1.1 |
| 16.50 | 5.36703 | 1.5 |
| 18.32 | 4.83823 | 100 |
| 19.22 | 4.6142 | 26.2 |
| 20.97 | 4.2325 | 1.5 |
| 21.67 | 4.0972 | 1.3 |
| 23.23 | 3.8266 | 1.3 |
| 24.50 | 3.63083 | 2.1 |
| 24.89 | 3.57407 | 1.6 |
| 30.72 | 2.90835 | 7.3 |

Figure 5:
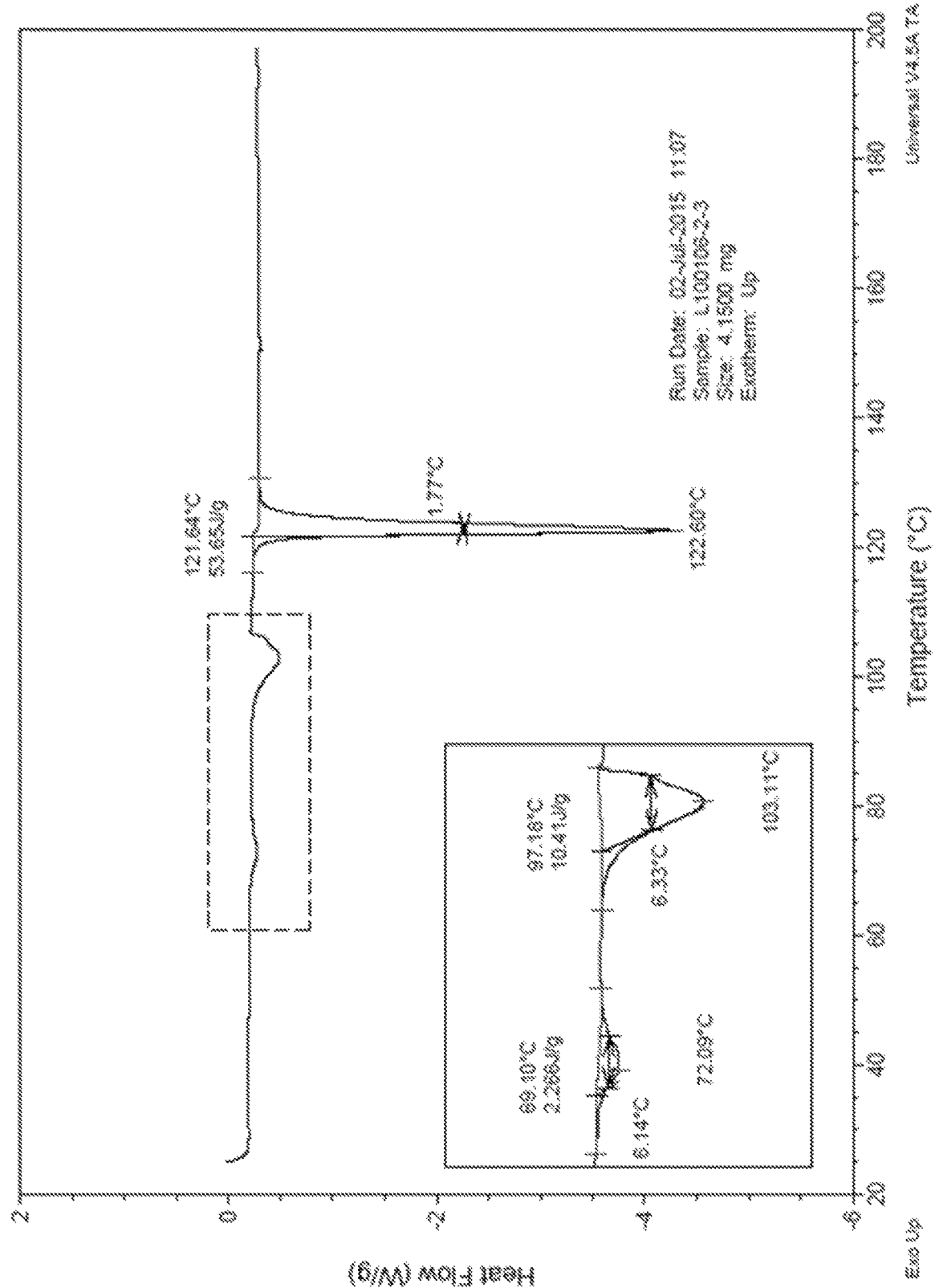
FIG. 5 depicts the characterization of Form B, prepared by Example 2, by differential scanning calorimetry (DSC).

DSC data were collected using a TA Instruments Q1000 DSC equipped with auto-sampler. Typically, samples (~2-7 mg) were placed in hermetic alodined aluminum sample pans and scanned from 30 to 180° C. at a rate of 10° C./min under a nitrogen purge of 50 mL/min. Results are depicted in FIG. 5.

Figure 6:
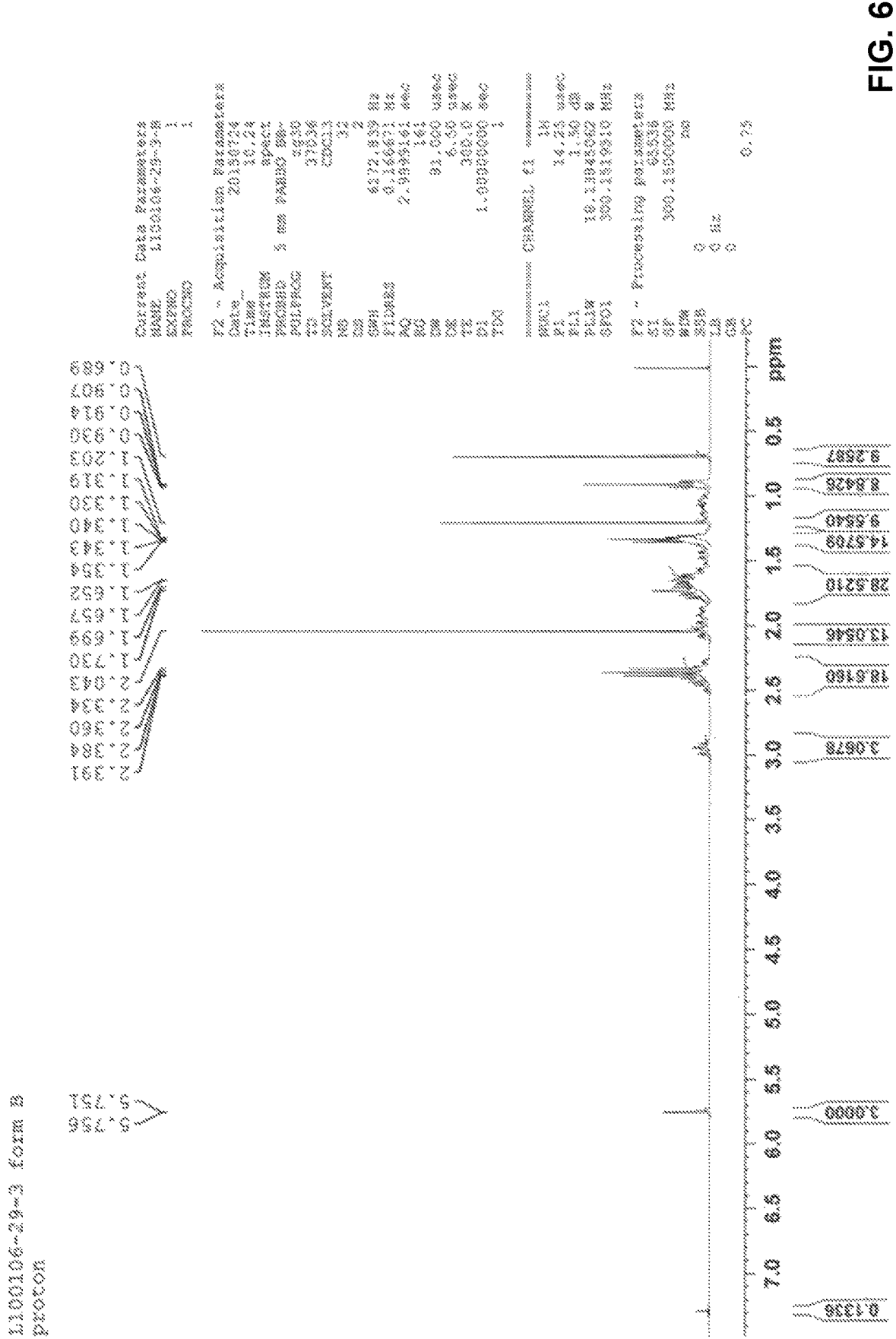
FIG. 6 depicts the $^1$H NMR spectrum of the dissolved crystal of Form B prepared by Example 2.

All endotherms present in the DSC traces point in the downward direction. The DSC of Form B showed a transition endothermic peak. Further XRD analysis showed that the observed endothermic peak is a result of conversion of Form B to Form A which melts upon further heating. Form B was analyzed using a hot stage microscope to determine the nature of the transition temperature at 105° C. It was observed that Form B melts and recrystallizes as Form A. $^1$H NMR was performed on a Bruker NMR spectrometer. Samples were prepared in deuterated chloroform. The spectrum is depicted in FIG. 6.

Example 3

Solution-mediated transformation studies were conducted to establish the relative physical stability of Form A and Form B versus temperature. Excess solid was suspended in a slurry using various solvents, including mixtures of benzyl benzoate and castor oil. After equilibration times of 1 day to two weeks, the excess solid was filtered and analyzed by powder x-ray diffraction to determine the crystalline form.

These experiments showed that Form A and B is part of an enantiotropic system with a transition temperature between 27° C. and 35° C. Above 35° C., Form A is more stable (less soluble) and below 27° C., Form B is more stable (less soluble). Additional studies demonstrated that Form B is likely to be more stable below room temperature.

Suspension formulations of HPC can therefore be made with Form B, as it is a physically stable polymorph for storage temperatures of room temperature (20-25° C.) or below (refrigeration).

Example 4—Amorphous Form

Figure 7:
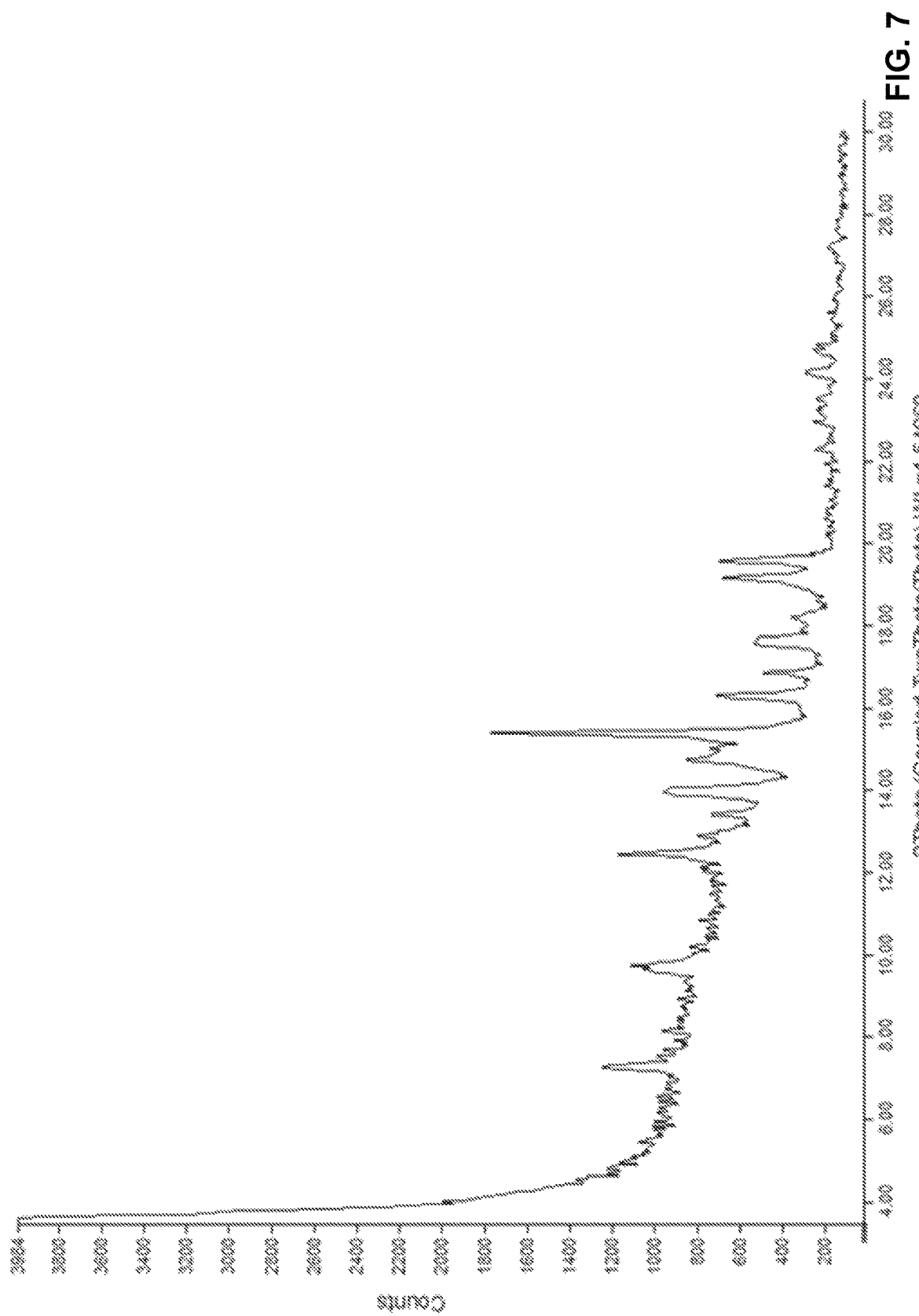
FIG. 7 depicts the X-ray diffraction pattern of amorphous material containing about 50% of Form A.

Amorphous material containing about 50% of Form A was prepared as follows:

Dry solid Form A was ground in a mortar and pestle for about 1 hour to yield a solid containing about 50% amorphous material with about 50% Form A. The amorphous content was calculated through dividing the total area of the baseline subtracted pattern by the area of the original pattern and then subtracting this value from unity. The result is multiplied by 100 to give amorphous percentage. The X-ray diffraction pattern of amorphous material containing about 50% of Form A is shown in FIG. 7.

Figure 8:
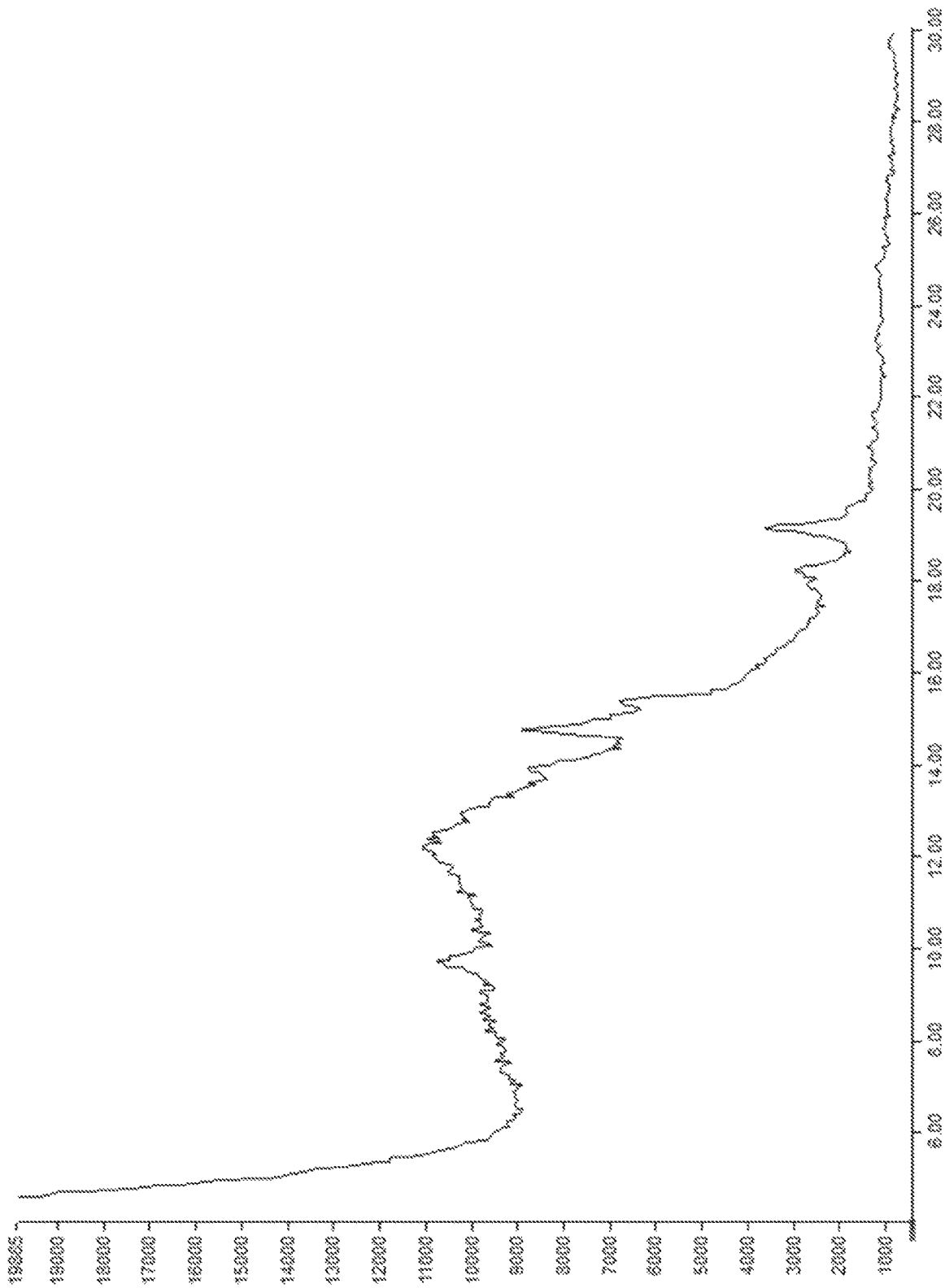
FIG. 8 depicts the X-ray diffraction pattern of amorphous material containing about 10% of Form B.

Amorphous material containing about 10% of Form B was prepared as follows:

Dry solid Form B was ground in a mortar and pestle for about 1 hour to yield a solid that was primarily amorphous with some traces of Form B. The amorphous content was calculated through dividing the total area of the baseline subtracted pattern by the area of the original pattern and then subtracting this value from unity. The result is multiplied by 100 to give amorphous percentage. The X-ray diffraction pattern of amorphous material containing about 10% of Form B is shown in FIG. 8.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A crystalline form of 17-α-hydroxyprogesterone caproate characterized by a powder X-ray diffraction pattern having a characteristic peak in degrees 2θ at about 9.6, 12.2, and 18.3 and a differential scanning calorimetry endothermic peak at about 100-105° C.

2. The crystalline form of claim 1, characterized by a powder X-ray diffraction pattern having characteristic peaks in degrees 2θ at about 9.6, 12.2, 13.9, 14.8, 15.4, 18.3, and 19.2.

3. The crystalline form of claim 1, characterized by a powder X-ray diffraction pattern having characteristic peaks in degrees 2θ at 9.6, 12.2, 13.0, 13.9, 14.8, 15.4, 18.3, and 19.2.

4. The crystalline form of claim 1, having the powder X-ray diffraction pattern shown in FIG. 4.

5. The crystalline form of claim 1, wherein the powder X-ray diffraction pattern was obtained using Cu Kα radiation.

6. A pharmaceutical composition comprising the crystalline form of claim 1, and a pharmaceutically acceptable excipient.

7. The pharmaceutical composition of claim 6, wherein the composition is a formulation for subcutaneous or intramuscular injections.

8. The pharmaceutical composition of claim 6, wherein the composition is a formulation for oral administration.

9. The pharmaceutical composition of claim 6, wherein the composition is a formulation for topical administration.

10. The pharmaceutical composition of claim 6, wherein the composition is a formulation for rectal or vaginal administration.

11. The pharmaceutical composition of claim 6, wherein the composition is a suspension of the crystalline form.

12. A drug substance comprising at least a detectable amount of the crystalline form of claim 1.

13. A drug substance comprising substantially pure crystalline form of claim 1.

14. The drug substance of claim 12, further comprising a crystalline form of 17-α-hydroxyprogesterone caproate characterized by a powder X-ray diffraction pattern having a characteristic peak in degrees 2θ at about 7.3.

15. A crystalline form of 17-α-hydroxyprogesterone caproate characterized by a powder X-ray diffraction pattern having a characteristic peak in degrees 2θ at about 9.6, 12.2, 13.9, 14.8, 15.4, 18.3, and 19.2.

16. A pharmaceutical composition comprising the crystalline form of claim 15, and a pharmaceutically acceptable excipient.

17. The pharmaceutical composition of claim 16, wherein the composition is a formulation for subcutaneous or intramuscular injections.

18. The pharmaceutical composition of claim 16, wherein the composition is a formulation for oral administration.

19. The pharmaceutical composition of claim 16, wherein the composition is a formulation for topical, rectal or vaginal administration.

20. The pharmaceutical composition of claim 16, wherein the composition is a suspension of the crystalline form.

21. A drug substance comprising at least a detectable amount of the crystalline form of claim 15.

22. A drug substance comprising substantially pure crystalline form of claim 15.

* * * * *